United States Patent [19]

McRae

[11] Patent Number: Plant 6,556

[45] Date of Patent: Jan. 24, 1989

[54] LILY PLANT NAMED CHARLESTON

[75] Inventor: Edward A. McRae, Boring, Oreg.

[73] Assignee: Melridge, Inc., Aurora, Oreg.

[21] Appl. No.: 50,858

[22] Filed: May 18, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new variety of hybrid lily plant bearing large clusters of flowers each of which is particularly characterized by its starry form with fluted tepal margins and a unique yellow/white/yellow color pattern, wherein the yellow appears as a flush at the central base portion of each tepal which is generally of an unmarked white color, the yellow color also appears at the tips of the tepals and on the edges of the tepal margins, and the flowers are of excellent form and long persistence both on the plant and as cut flowers. This combination is completely new in the upright Asiatic divisions of lilies suited to forcing and to mass commercial cultivation. The plant is highly resistant to disease and shows high tolerance of virus, making it an excellent garden plant, and its bulbs may be precooled and forced for cut flower production producing a vigorous clone that is a good grower and propagator.

1 Drawing Sheet

BACKGROUND OF THE INVENTION

This new variety of lily plant originated as a seedling selected from a group of seedlings planted by me in the course of breeding efforts at Sandy, Oreg., with the object of producing lilies in yellow, cream and white color tones well suited to forcing for cut flower production out-of-season, heretofore unknown in the lily breeding art. The planting from which the present variety was selected was done with seeds derived from a hybrid resulting from my crossing of a yellow flowered seedling selected from the cross of 'Connecticut King' (unpatented) and 'John Evans' (unpatented), as the seed parent, and as the pollen parent, an orange/white bicolored seedling selected from the cross of 'Connecticut King' and 'Enchantment' (unpatented). This plant was selected for propagation and test because of its large flowers of "starry" form and a distinctive yellow/-white/yellow color pattern, quite unique in this type of lily, and this selected seedling was asexually reproduced by me, as well as under my direction, at Sandy, Oreg., with such success that propagation was continued through several successive generations both by bulb scale propagation and by natural propagation from bulblets, which demonstrated clearly that the novel and distinguishing characteristics of this new lily variety would hold true from generation to generation and appeared to be firmly fixed.

DESCRIPTION OF THE DRAWING

My new variety of lily plant is illustrated by the accompanying photographic drawing, which shows a face view of an open bloom in full color and illustrates the flower form, the tepal arrangement and in particular, the novel and distinguishing yellow/white/yellow color pattern; the color rendition being as nearly true as it is reasonably possible to obtain by professional photographic procedures.

DESCRIPTION OF THE NEW VARIETY

The following is a detailed description of my new variety of hybrid Asiatic lily with nomenclature according to The International Lily Register (The Royal Horticultural Society of London, England, Second Edition, 1969) and with color designations according to The R.H.S. Colour Chart published by The Royal Horticultural Society in 1966.

THE PLANT

Origin: Seedling.

Parentage:

- *Seed parent.*—A yellow flowered seedling selected from the cross of 'Connecticut Kind' and 'Jones Evans' (both unpatented).
- *Pollen parent.*—An orange/white bicolored seedling selected from the cross of 'Connecticut King' and 'Enchantment'.

Classification:

- *Botanic.*—Division I-A, Upright Asiatic Hybrid Lily, according to The Horticultural Classification of Lilies, The Royal Horticultural Society of London.
- *Commercial.*—Hybrid Lilium Clone.

Form: Single stem, erect and stately.

Height: About 70 to 85 cm. for stems produced by glasshouse forcing of bulbs of about 15 to 18 cm. in circumference, provided that their light levels are adequate; low light levels may cause "stretching". Bulbs in their second year of growth after scale propagation in the field produce stems averaging about 100 cm. tall.

Growth: Vigorous and upright.

Foliage:

- *Quantity.*—Abundant.
- *Leaf size.*—About 7 to 10 cm. long and about 6 to 15 mm. wide.
- *Leaf shape.*—Lanceolate with acuminate tip.
- *Texture.*—Leathery and glabrous.
- *Aspect.*—Glossy.
- *Color.*—Medium green on the upper side and somewhat lighter on the lower side.

Bulbs:

- *Size.*—Varying, ranging up to 25 cm. in circumference as commercially used.
- *Color.*—White.

THE BUD

Form: Long ovoid with obtuse tip and ovate base.

Size: About 8 to 9 cm. long and about 7 cm. in circumference just prior to opening.

Opening rate: The bud opens slowly, taking about one hour in response to morning light.

Color: Soft yellow, 2C, shading into white at the base and at the apex just prior to opening and as the tepals unfurl.

Peduncle:

*Length.*—Averages about 4 to 6 cm., but may elongate if light levels are too low or if the bulbs have been improperly stored prior to forcing.

*Color.*—Medium green with plum overlay.

THE FLOWER

Blooming habit: Once annually and profusely in midseason.

Size: Large; about 15 to 19 cm. in diameter.

Borne: In a single raceme having 8 to 12 buds, from a bulb about 12 to 15 cm. in circumference.

Shape: Cup-shaped upon first opening and flattening as the tepals recurve during the second day.

Tepalage:

*Number.*—Six, widely spaced in hexagonal arrangement.

*Size.*—The outer tepals are about 2 to 2.5 cm. wide and the inner tepals are about 2.5 to 3 cm. wide. The tepal length is about 7 to 8 cm. and the tepals do not overlap thereby producing a starry appearance. The tepal margins are fluted and the tepals are slightly cupped.

*Color.*—The base color is a clear white and there is a flush of yellow, 12A, about 1 to 2 cm. wide extending from 2 to 3 cm. from the nectaries along the center of each tepal. A band of the same color about 1 mm. wide extends along the tepal margins and there is an additional flush of the same yellow color about 3 to 4 mm. wide and about 2 to 4 mm. long at the apex of each tepal. The nectary is a soft green furrow and its border is light pubescent and white.

*Spotting.*—The tepals vary from bearing no spots to having 5 to 15 extremely tiny and inconspicuous spots parallel with the nectaries.

*Aspect.*—The flower is shiny.

*Color changes.*—The white portion of the flower may deepen to soft cream and the yellow portion may deepen to about 13A-B as the flower ages. Color changes are inconspicuous if the light levels are adequate for cut flower maintenance.

*Longevity.*—The tepals stay on the stems for about three weeks.

Pedicel:

*Length.*—Averages about 3 to 10 cm.

*Color.*—Medium green with plum overlay.

*Form.*—Sturdy and ascending upwardly to about 45 degrees from the horizontal. The occurrence of secondary buds is very rare.

*Color.*—Medium green with plum overlay.

Disease resistance: The flower and plant are resistant to disease; and in particular, they are resistant to Fusarium bulb rot and Botrytis blight.

Fragrance: None.

Lasting quality: The flower is long lasting both on the plant and as a cut flower.

REPRODUCTIVE ORGANS

Stamens:

*Number.*—Six.

*Arrangement.*—Typical of genus Lilium.

*Anthers and pollen (dehisced).*—Yellow-Orange, 23B.

*Filaments.*—Length: About 5 cm. Color: Soft yellow, 12C.

Pistils:

*Number.*—One.

*Length.*—About 5 cm.

*Stigma.*—Color: Soft yellow, 12B, occasionally overlaid with plum.

Characteristics of ovary: The ovary has the characteristics of the genus Lilium.

THE FRUIT

Fertility: The fruit is fertile.

Shape: Ovoid.

Color at maturity: Soft brown, sometimes overlaid with soft plum.

This new variety of lily is distinctively different from any presently available cultivar. It somewhat resembles 'Connecticut King' but it has a unique yellow/white/yellow color pattern whereas 'Connecticut King' is a solid yellow.

I claim:

1. The new and distinctive variety of Asiatic hybrid lily plant and parts thereof, substantially as herein shown and described, characterized by its large "starry" flower form having fluted tepal margins and a distinctive yellow/white/yellow color pattern: the excellence of its flower form, and its versatility both as a garden plant and as a cut flower producer from precooled bulbs forced out-of-season under glass.

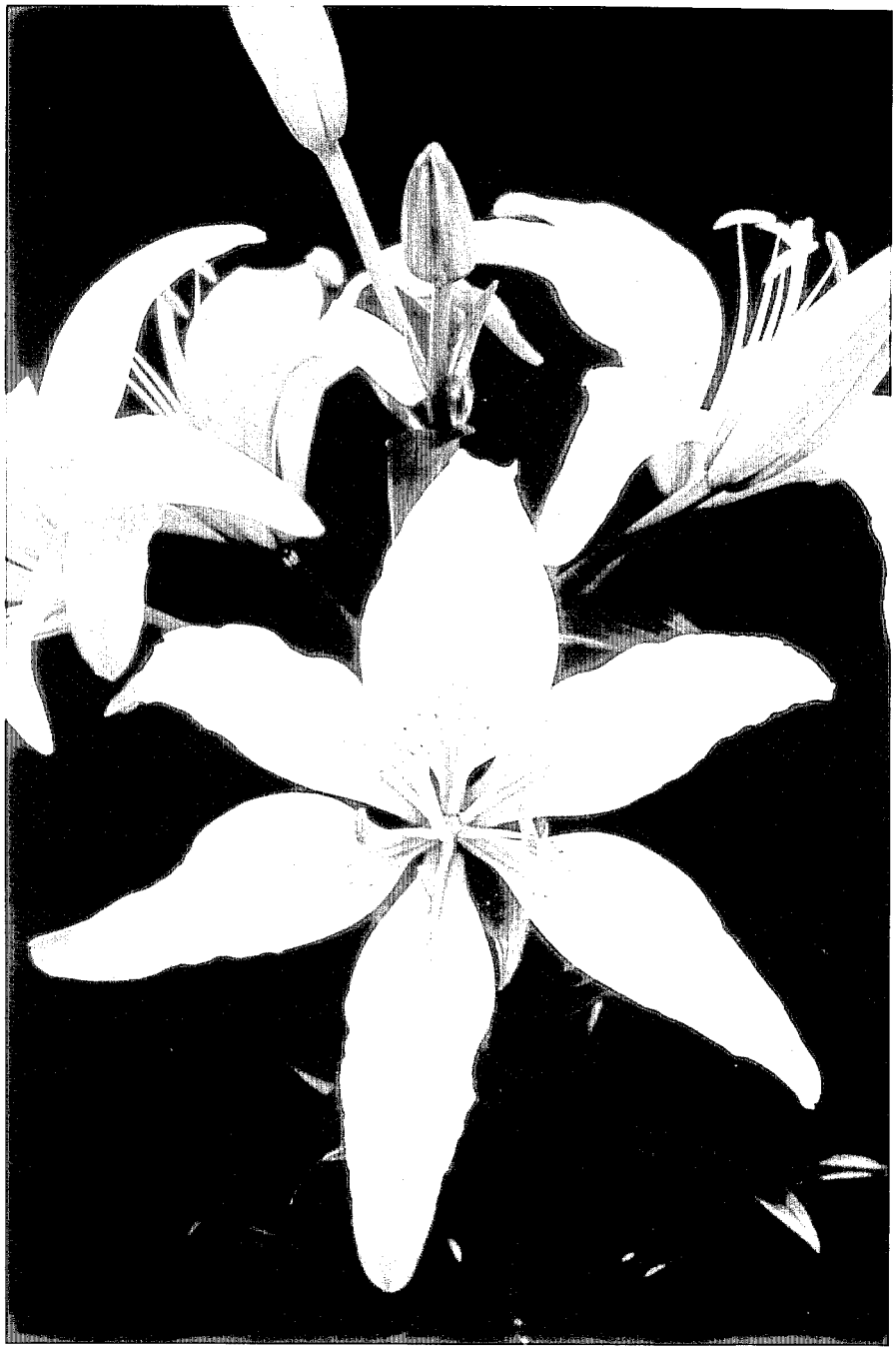

* * * * *